(12) United States Patent
Plishner

(10) Patent No.: US 7,395,166 B2
(45) Date of Patent: *Jul. 1, 2008

(54) CONNECTOR INCLUDING AN INTEGRATED CIRCUIT POWERED BY A CONNECTION TO A CONDUCTOR TERMINATING IN THE CONNECTOR

(75) Inventor: Paul J. Plishner, 42 Foster Crossing, Southampton, NY (US) 11968

(73) Assignee: Paul J. Plishner, Southampton, NY (US)

( * ) Notice: Subject to any disclaimer, the term of this patent is extended or adjusted under 35 U.S.C. 154(b) by 120 days.

This patent is subject to a terminal disclaimer.

(21) Appl. No.: 11/444,905

(22) Filed: May 31, 2006

(65) Prior Publication Data

US 2006/0265142 A1    Nov. 23, 2006

Related U.S. Application Data

(63) Continuation of application No. 10/840,752, filed on May 6, 2004.

(51) Int. Cl.
*H01R 13/00* (2006.01)
(52) U.S. Cl. .................... 702/108; 439/620.15; 324/754
(58) Field of Classification Search ................. 702/108; 439/620.15, 668, 675, 95
See application file for complete search history.

(56) References Cited

U.S. PATENT DOCUMENTS

| | | | |
|---|---|---|---|
| 3,154,360 A | 10/1964 | Plishner | |
| 3,983,546 A | 9/1976 | Zappe | |
| 4,038,625 A | 7/1977 | Tompkins et al. | ............. 336/83 |
| 4,161,692 A | 7/1979 | Tarzwell | ..................... 324/754 |
| 4,839,854 A | 6/1989 | Sakami et al. | ................. 710/1 |
| 4,862,231 A | 8/1989 | Abend | .......................... 257/81 |
| 5,006,793 A | 4/1991 | Gleason et al. | ............. 324/754 |
| 5,054,112 A | 10/1991 | Ike | ............................. 455/41.1 |
| 5,432,486 A | 7/1995 | Wong | ......................... 333/109 |
| 5,629,838 A | 5/1997 | Knight et al. | |

(Continued)

FOREIGN PATENT DOCUMENTS

DE         27 52 783         1/1979

(Continued)

OTHER PUBLICATIONS

T. Mangold et al., "A multichip module integration technology on silicon substrate for high frequency applications," 4 pages.

(Continued)

*Primary Examiner*—John E Barlow, Jr.
*Assistant Examiner*—Hien Vo
(74) *Attorney, Agent, or Firm*—Ware, Fressola, Van Der Sluys & Adolphson LLP

(57) ABSTRACT

A connector including an integrated circuit, for connecting two conductors directly or indirectly. The integrated circuit derives power either from one of the connectors being connected by the connector or from one or more other conductors terminating in the connector, and not from a battery or photovoltaic cell or other such voltage source. A coupler connected to the integrated circuit is used in case of an indirect connection of the two conductors and/or of the one or both of the conductors to the integrated circuit, to avoid having to make a physical attachment.

28 Claims, 8 Drawing Sheets

U.S. PATENT DOCUMENTS

| | | | | |
|---|---|---|---|---|
| 5,692,925 | A | 12/1997 | Bogese | 439/620 |
| 5,786,979 | A | 7/1998 | Douglass | 361/328 |
| 5,943,199 | A | 8/1999 | Aromin | |
| 5,977,773 | A | 11/1999 | Medelius et al. | |
| 6,354,865 | B1 | 3/2002 | Bogese | 439/418 |
| 6,416,334 | B1 | 7/2002 | Plishner | |
| 6,449,308 | B1 | 9/2002 | Knight, Jr. et al. | |
| 6,496,889 | B1 | 12/2002 | Perino et al. | |
| 6,500,696 | B2 | 12/2002 | Sutherland | |
| 6,572,402 | B2 | 6/2003 | Lin | 439/490 |
| 6,612,852 | B1 | 9/2003 | Panella | |
| 6,764,347 | B1 | 7/2004 | Plishner | 439/668 |
| 6,773,306 | B2 | 8/2004 | Plishner | 439/620 |
| 6,891,447 | B2 | 5/2005 | Song | 333/24 R |

FOREIGN PATENT DOCUMENTS

| | | |
|---|---|---|
| EP | 0 573 714 | 12/1993 |
| EP | 0 676 710 | 10/1995 |
| EP | 1 206 012 | 5/2002 |
| GB | 2 237 129 | 4/1991 |
| WO | WO 2004/012265 | 2/2004 |

OTHER PUBLICATIONS

N. Rinaldi et al., "U.C.A.N.'s ultra wide band system: baseband algorithm design," Apr. 2003, 6 pages.

O. Albert et al., "Low-power ultra-wideband radio testbed for short-range data transmission," 6 pages.

N. M. Khan et al., "Use of state-space approach and Kalman filter estimation in channel modeling for multiuser detection in time-varying environment," 5 pages.

A. L. Sigvartsen, "Inside the AMD Hammer microprocessor—AMD's next generation microprocessor architecture (Fred Weber)," Oct. 22, 2001, infosatellite.com/news, 15 pages.

D. Salzman et al., "Manufacturability of capacitively coupled multichip modules," IEEE Transactions on Components, Packaging and Manufacturing Technology—Part B, vol. 18, No. 2, May 1995, pp. 277-281.

D. Salzman et al., "Application of capacitive coupling to switch fabrics," IEEE 1994, pp. 195-199.

The New York Times, (nytimes.com), Apr. 8, 2004, What's Next Refining Semiconductors, One Atom at a Time, By Anne Eisenberg, (as published on the Internet).

Quantum Entanglement from Wikipedia, the free encyclopedia, web page en.wikipedia.org, (as published on the Internet).

Gridpoints the Quarterly Publication of the Numerical Aerospace Simulation Systems Divison, Summer 2000, NAS researchers are developing atomic scale transistors to enable future microelectronics (see p. 10). web page www.nas.nasa.gov/gridpoints, (as published on the Internet).

AMBIT Corporation, Nanotechnology, Antenna Systems, and Pressures . . . , carbon nanostructures, web page at ambitcorp.com, (as published on the Internet).

D. Salzman et al., "Capacitively coupled multichip modules," MCM '94 Proceedings, pp. 487-494.

M. F. Chang et al., "RF/wireless interconnect for inter- and intra-chip communications," Proceedings of the IEEE vol. 89, No. 4, Apr. 2001, pp. 456-466.

J. D. Meindl et al., "Interconnecting device opportunities for gigascale integration (GSI)," IEEE 2001, pp. 23.1.1-23.1.4.

D. Salzman et al., "Capacitive coupling solves the known good die problem," IEEE 1994, pp. 95-100.

R. Yung et al., "Future trend of microprocessor design (invited paper)," ESSCIRC 2002, pp. 43-46.

M. Kuijk et al., "Integration of CMOS-VSLI and light emitting sources by capacitive coupling," Electronics Letters, Oct. 9, 1997, vol. 33, No. 21, 2 pages.

R. J. Drost et al., "Proximity communication," IEEE 2003 Custom Integrated Circuits Conference, pp. 469-472.

S. Mick et al., "4 Gbps high-density AC coupled interconnection (invited paper)," IEEE 2002 Custom Integrated Circuits Conference, pp. 133-140.

K. Kanda et al., "1.27 Gb/s/pin 3mW/pin wireless superconnect (WSC) interface scheme," ISSCC 2003/Session 10/High Speed Building Blocks/Paper 10.7, IEEE 2003 International Solid-State Circuits Conference, 10 pages.

Quantum Entanglement from Wikipedia, the free encyclopedia, web page en.wikipedia.org, (as published on the Internet). (Jul. 1, 2004).

AMBIT Corporation, Nanotechnology, Antenna Systems, and Pressures . . . , carbon nanostructures, web page at ambitcorp.com, (as published on the Internet). (2004).

Dec. 2002 issue of Microwave Journal, advertisement in.

Dec. 2002 issue of Microwave Products Digest, advertisement in.

Dec. 2002 issue of Maritime Reporter, advertisement in.

Estimated Dec. 2002 issue of Microwave Products Digest, advertisement in.

News & Views, Nanotubes Strong Bundled, Natures Materials 3, 136-136 (Mar. 2004), (as published on the Internet).

Sasaki et al., A compact optical active connector and optical interconnect module with an electrical connector interface, IEEE transactions on advance packaging, vol. 22, No. 4, Nov. 1999, pp. 541-550.

Sasaki et al. , IEEE, 1996 Electrical components and technology conference, pp. 512-519.

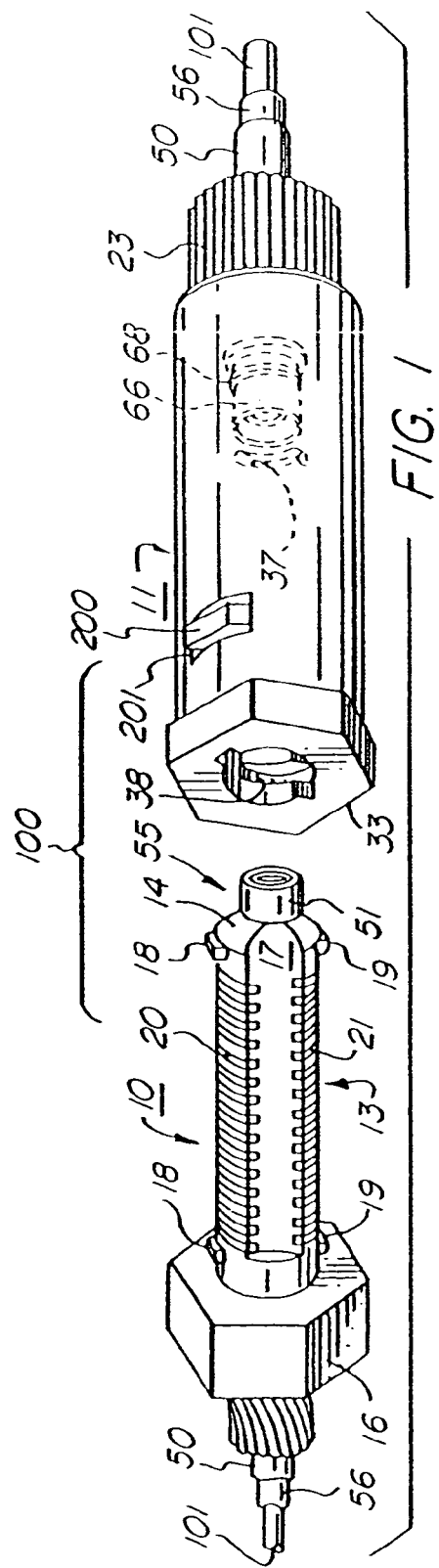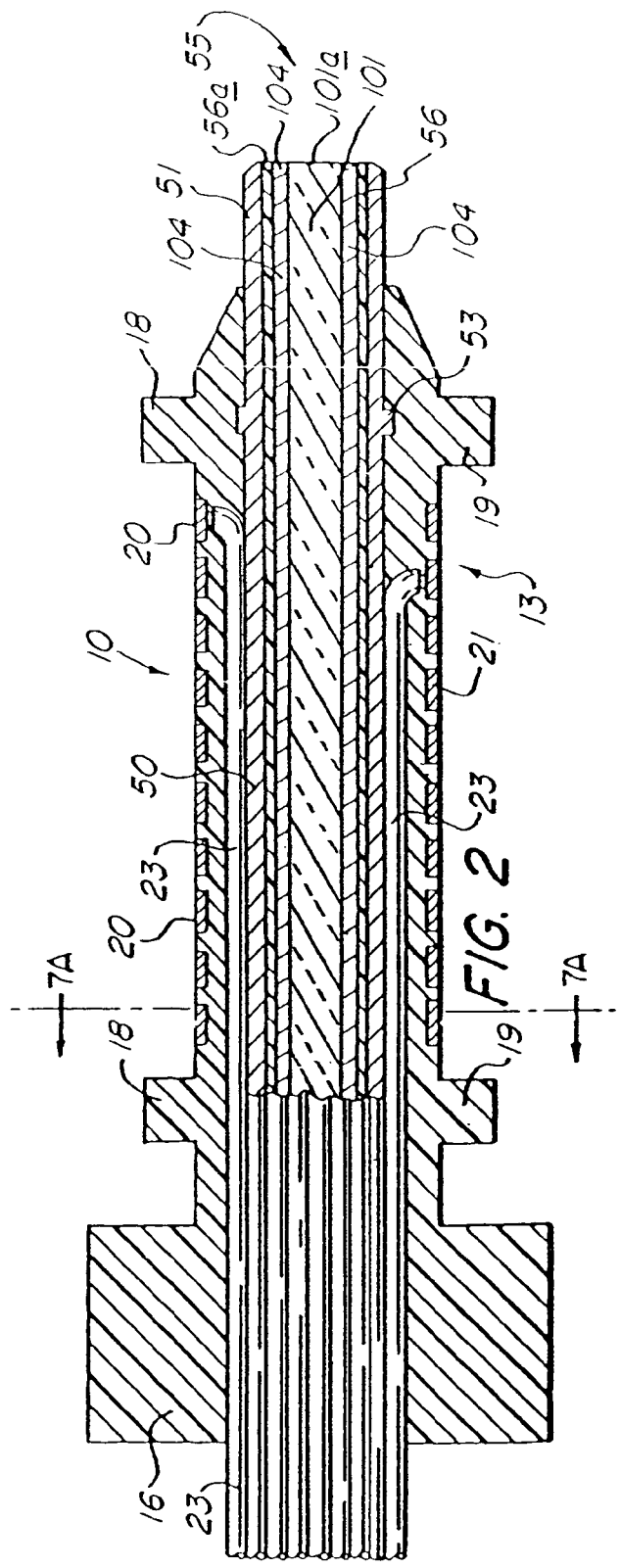

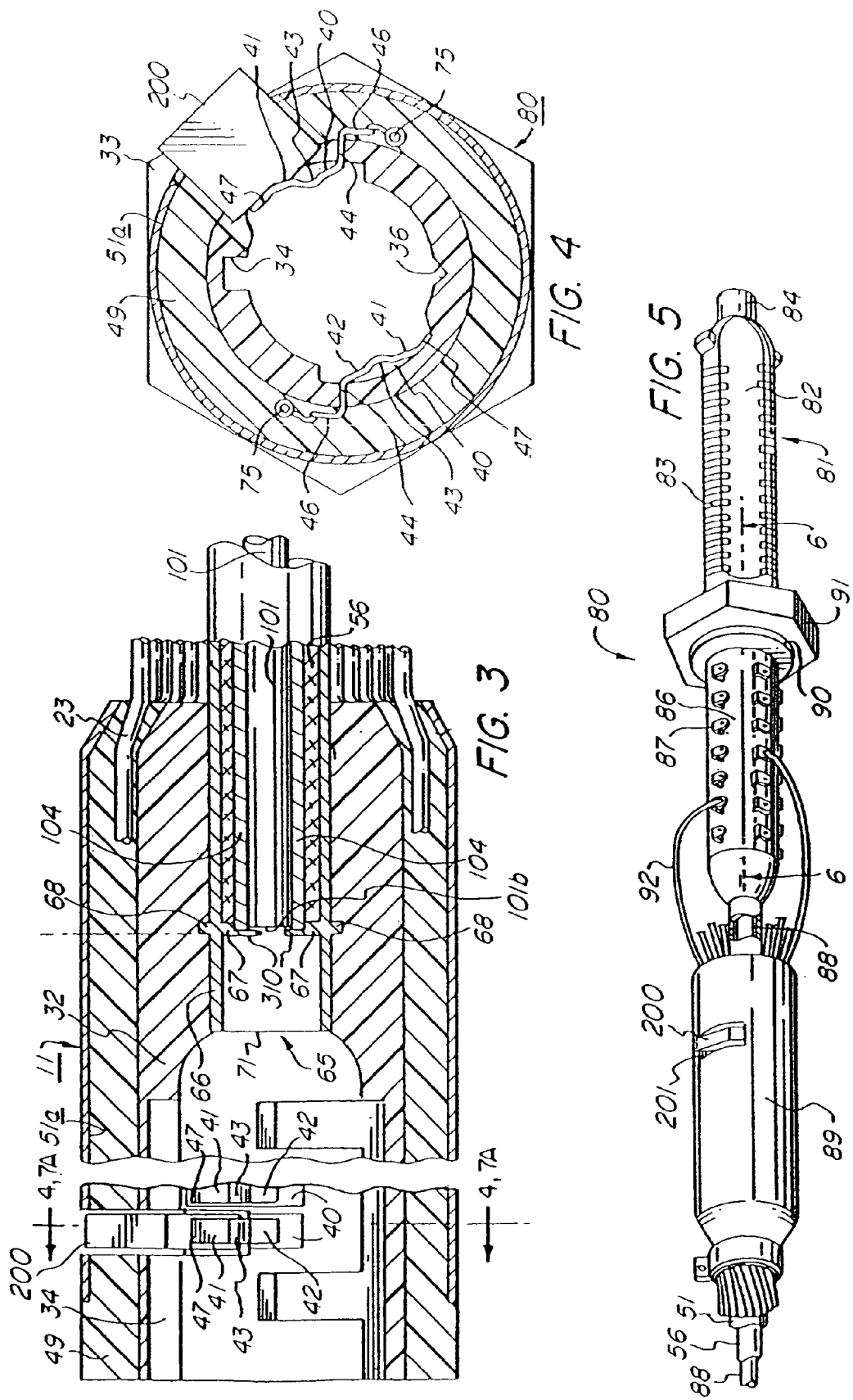

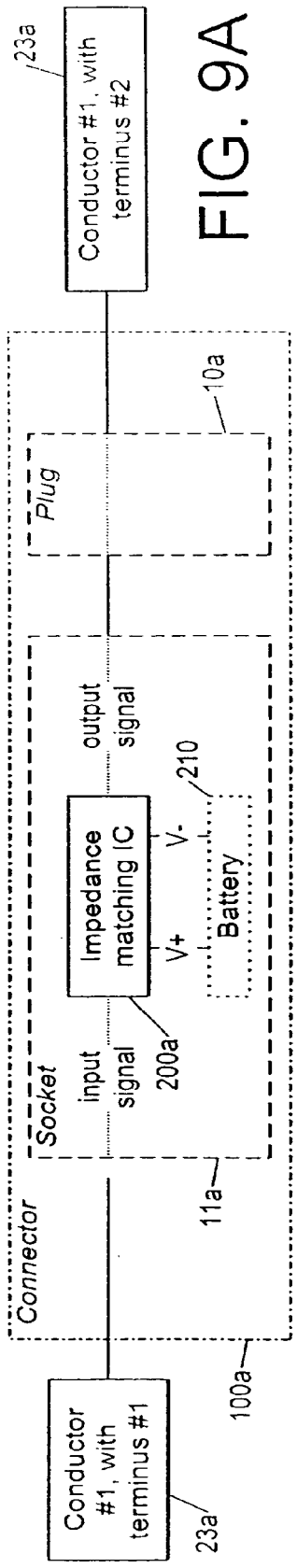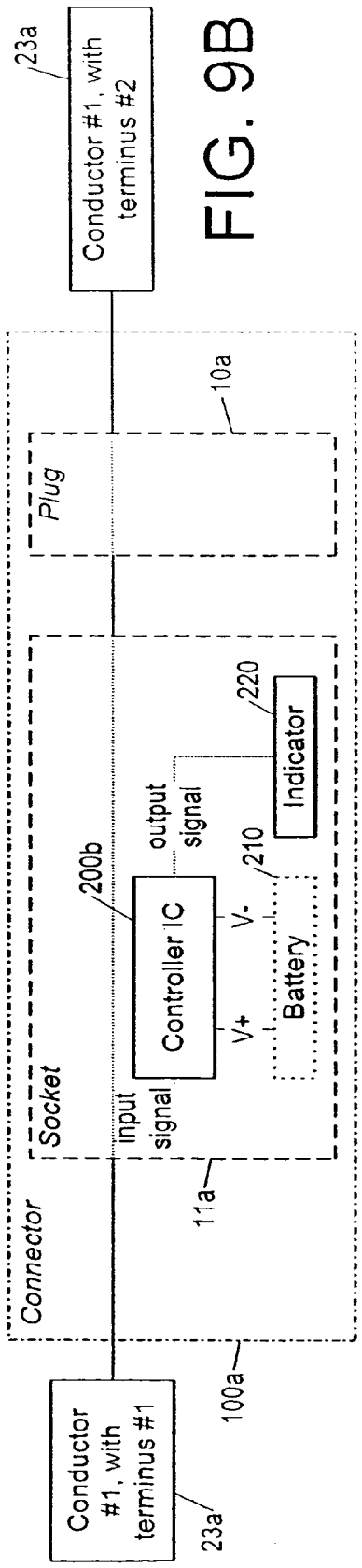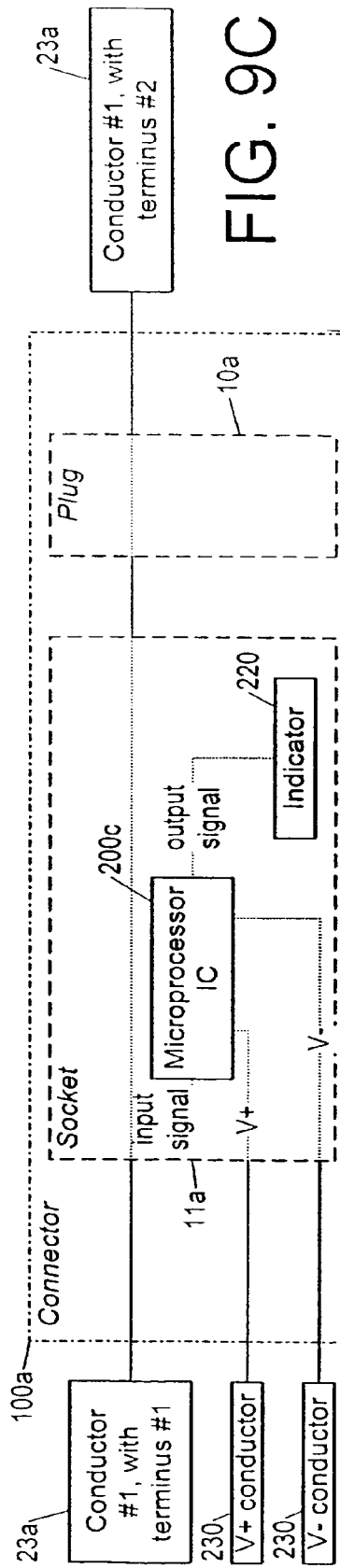

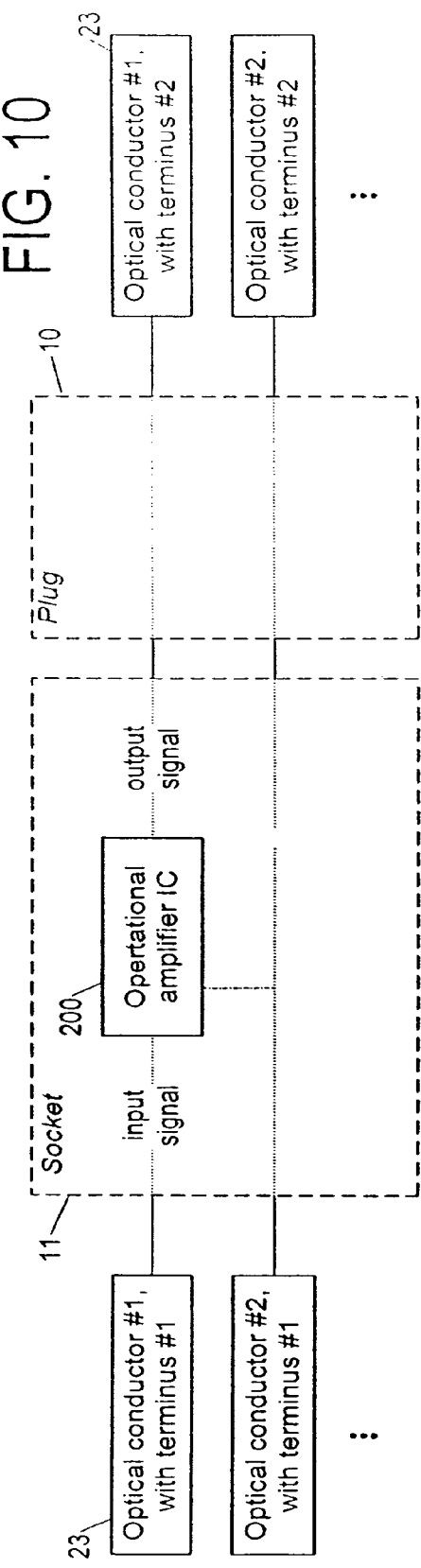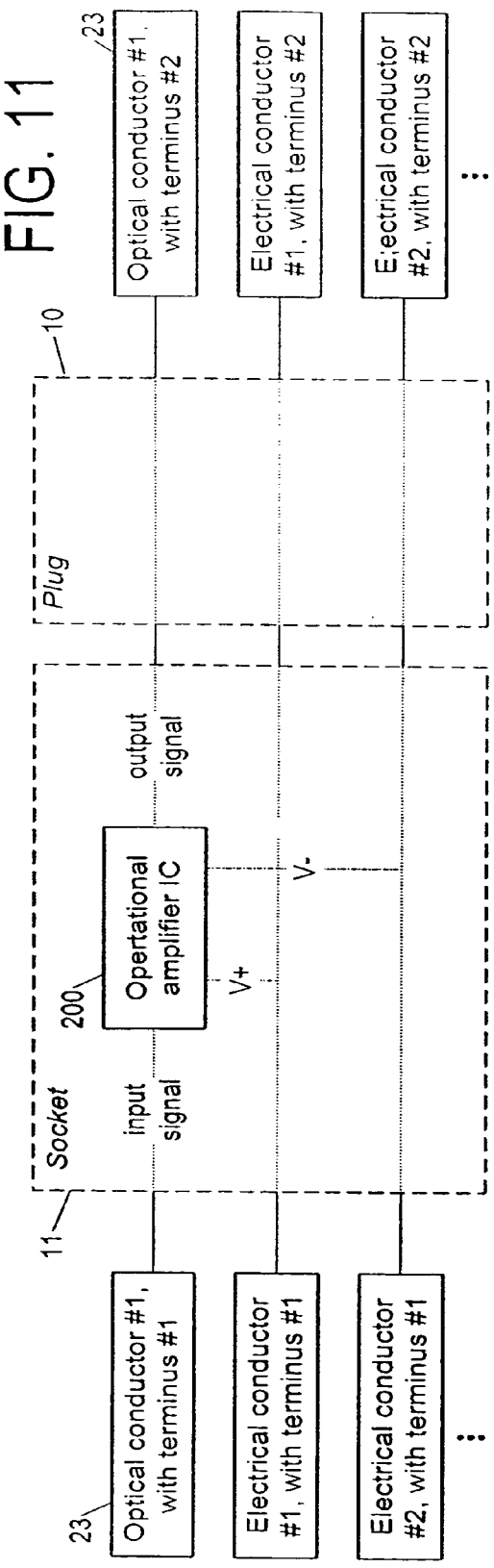

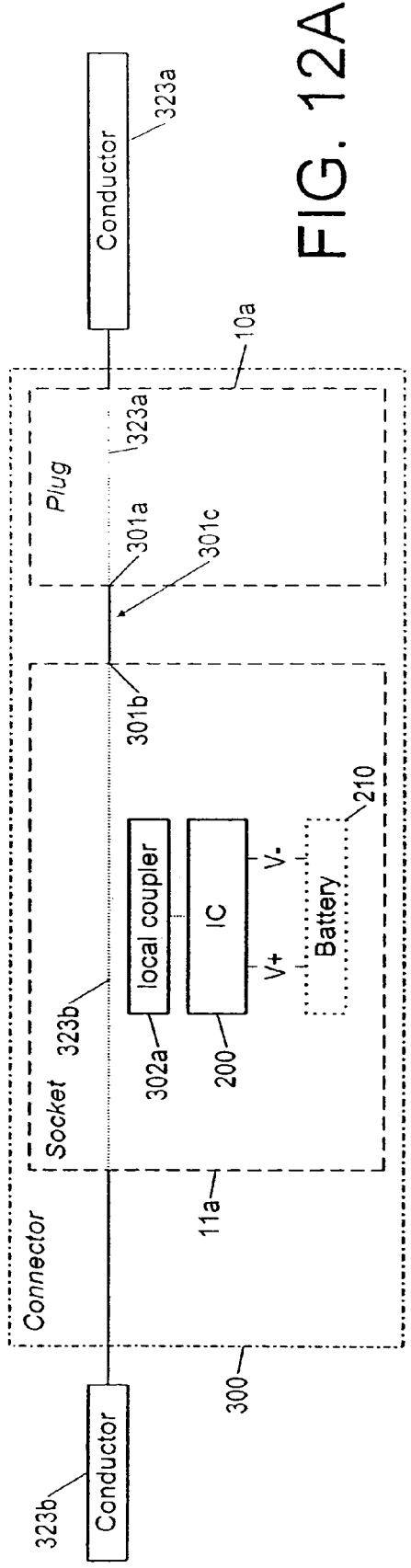
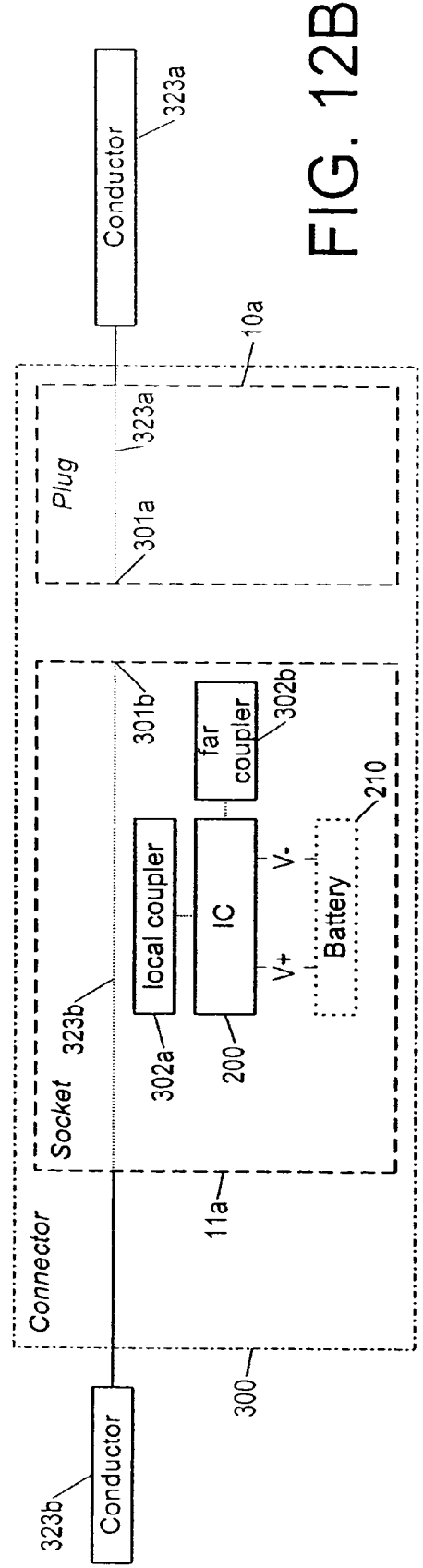

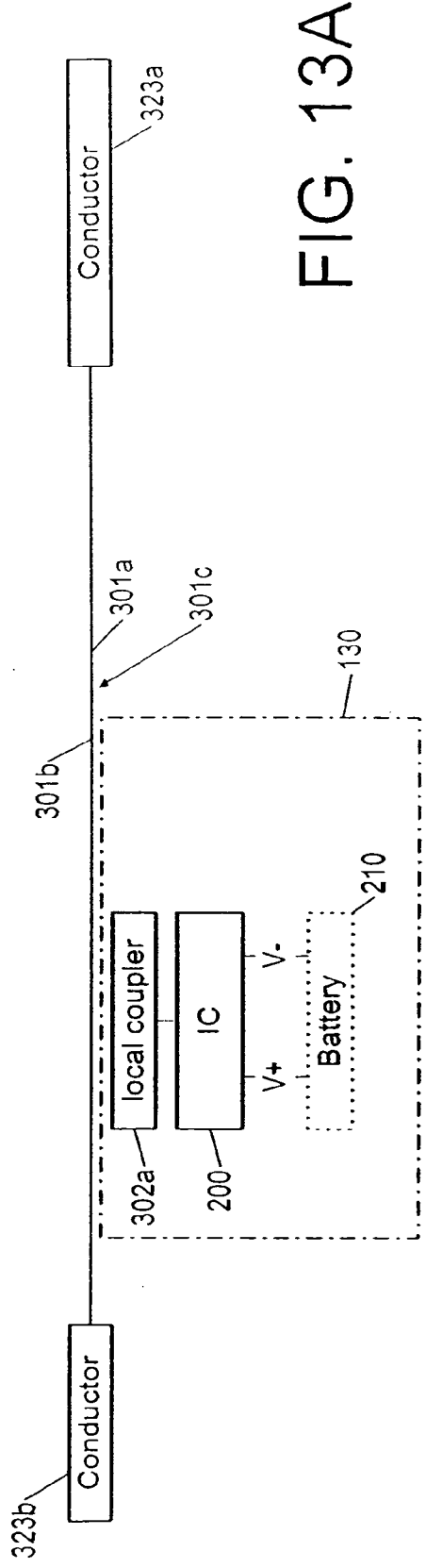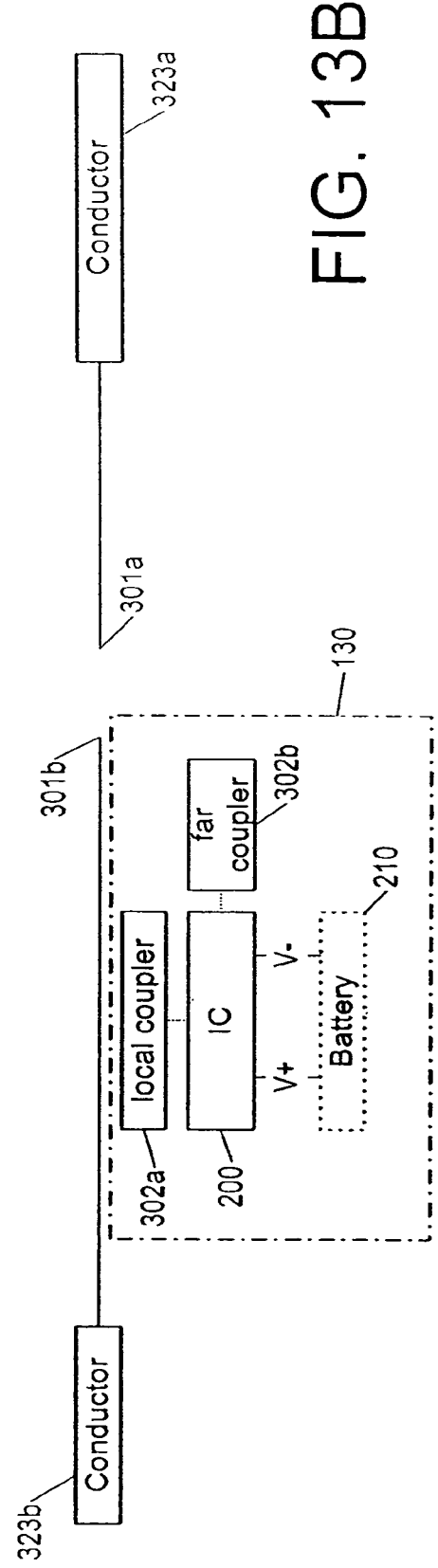

CONNECTOR INCLUDING AN INTEGRATED CIRCUIT POWERED BY A CONNECTION TO A CONDUCTOR TERMINATING IN THE CONNECTOR

RELATED APPLICATIONS

This application is a continuation of U.S. application Ser. No. 10/840,752 filed May 6, 2004.

FIELD OF THE INVENTION

The present invention pertains to the field of circuits for electrical and optical signals and having integrated circuits (ICs) as components of the circuits, including ICs embedded in connectors for electrical and optical signal-bearing lines.

BACKGROUND OF THE INVENTION

The prior art provides many types of connectors for connecting electrical or optical conductors. In addition, multi-element electrical connectors for simultaneously connecting several low frequency (including DC) current-carrying conductors (i.e. two electrical lines each including several current-carrying conductors) are well known in the art. The prior art further includes a multi-conductor/coaxial electrical connector for simultaneously connecting a multi-conductor and a coaxial cable. For example, U.S. Pat. No. 3,154,360 provides a plug member and a socket (receptacle) member. The prior art also includes connectors for connecting optical fibers, and even connectors for simultaneously connecting several low frequency current-carrying conductors (including DC) and also two or more ends of optical fiber, as disclosed in U.S. Pat. No. 6,416,334.

In addition, integrated circuits (ICs) are well known in the art; the prior art teaches providing integrated circuits (ICs) for performing numerous different functions. ICs are available for use as voltage or current amplifiers, for test and evaluation of circuits, for use as elements of computers, for control, for use in connection with optical circuits (e.g. for performing one or another task of an add/drop multiplexer in a wavelength division multiplex signal), and for providing numerous other useful functions.

In many applications in which two or more conductors of one or more types of signal are used, it is often necessary to perform one or another kind of function at the location where the conductors are connected. For example, it would be useful to provide impedance matching at the point at which two conductors are joined. In addition, it is often useful to amplify a signal at a connector, using either an analog signal amplifier or a digital signal amplifier, or in a purely analog application, provide for either current or voltage amplification. In other applications, other kinds of functions would advantageously be performed at the point of connection of two or more conductors or one or more types.

What is needed therefore is a connector providing not only for connection of two or more conductors or one or more types of conductor, but also providing useful functions having to do with either the signals being conveyed by the connectors, or with the connection itself (including, e.g. test and evaluation of the connection).

Further, for ease of repair in the field and for other reasons affecting performance, it is advantageous to provide for useful functions in a connector not by ICs provided so as to make a physical connection with the conductors being connected by the connector, but instead indirectly coupled, i.e. coupled without making a physical connection to the lines/conductors being connected. Further, such indirectly coupling would be advantageous not only in case of connectors, but in case of electrical and optical circuits generally.

SUMMARY OF THE INVENTION

In accord with at least some of the above-mentioned objects, a connector is provided having a first and second housing and including an integrated circuit mechanically attached to or included in the first housing, and directly or indirectly connected to a conductor received by the first housing, and the connector is configured to use as a supply voltage for the integrated circuit a voltage provided at least in part from the connection to the conductor or from a connection to another conductor received by the first housing.

BRIEF DESCRIPTION OF THE DRAWINGS

The above and other objects, features and advantages of the invention will become apparent from a consideration of the subsequent detailed description presented in connection with accompanying drawings, in which:

FIG. 1 is a perspective view of a connector embodying the present invention and so including an embedded integrated circuit and also including a plug section and a socket section illustrated in an uncoupled condition.

FIG. 2 is a medial longitudinal sectional view of the plug section.

FIG. 3 is a fragmentary medial longitudinal sectional view of the socket section.

FIG. 4 is a sectional view taken along line 4-4 in FIG. 3.

FIG. 5 is an exploded perspective view of a modified form of a plug according to the invention, as an example of the use of the invention in any connector.

FIGS. 9A-C are block diagrams illustrating different examples of connectors according to the invention.

FIG. 10 is a block diagram of a connector having an integrated circuit physically connected to and in series with an optical conductor and powered by tapping another optical conductor.

FIG. 11 is a block diagram of a connector having an integrated circuit physically connected to and in series with an optical conductor as in FIG. 10, but powered by tapping two electrical conductors.

FIGS. 12A-B are block diagrams illustrating embodiments of a connector according to the invention in which an embedded integrated circuit is electromagnetically (including optically) but not mechanically coupled to one or more of the conductors in a pair of conductors being connected by the connector.

FIGS. 13A-B are block diagrams illustrating embodiments of an apparatus according to the invention in which an integrated circuit is electromagnetically (including optically) but not mechanically coupled to one or more conductors.

BEST MODE FOR CARRYING OUT THE INVENTION

The invention will now be described as a connector for simultaneously connecting several low frequency current-carrying (electrical) conductors (including DC) and also two or more ends of optical fiber (i.e. an optical conductor), and including an embedded operational amplifier type of integrated circuit (IC) for use in amplifying a voltage signal conveyed by one of the conductors. It should be understood, however, that the invention comprehends any kind of connector, including any kind of splice, with one or more of any type of IC embedded in it, not only operational amplifiers. Also, it should be understood that the terminology "embedded integrated circuit" is used here to encompass an integrated circuit electrically and also physically attached to or embedded in a connector so as to be a part of, or integral with, the connector, and also an integrated circuit actually buried in the material of the housing or casing of the connector. ICs that are, according to the invention, advantageously embedded in a connector include ICs for performing tasks in connection with the function of either an optical or an electrical circuit or optoelectronic chips—especially those now being developed to use so-called surface plasmon polaritons (SPPs), which are neither photons nor electrons but rely on both for their existence and bridge the gap between the two, i.e. make it possible for electrons and photons to interact meaningfully in a chip. Examples of ICs that are, according to the invention, advantageously embedded in a conductor are: voltage or current or signal amplifier ICs, ICs for test and evaluation of circuits, ICs for use as elements of computers, for control, for use as or in connection with add/drop multiplexers in a wavelength division multiplex signal, for use as optical logic gates, for use in impedance matching and in simple throughput signal amplification, for use as optical packet switches, for use as LED switches, for use as wavelength division multiplexers, for use as memory buffers, for use as analog to digital converters, for use as voltage regulators, for use as LED switches, for use as data traffic routers, for use as demultiplexers for crosstalk suppression, for use as optical parametric amplifiers, for use as optical clock for signal processing, ICs for use as repeaters for reading and recreating digital signals, and ICs for use in SPP switching.

Figure 6:
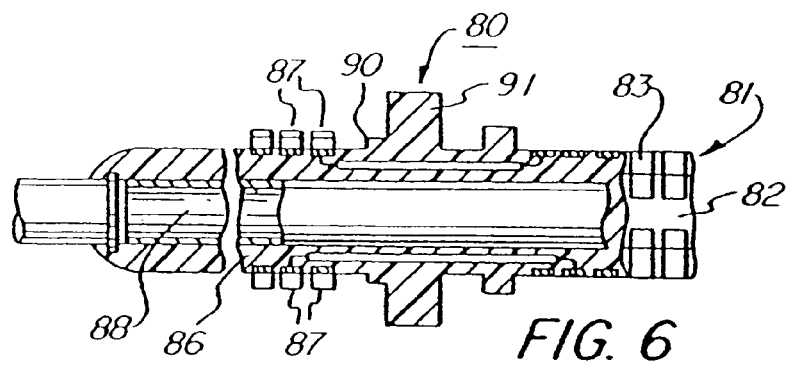
FIG. 6 is a fragmentary sectional view taken along line 6-6 in FIG. 5.
Figure 7A:
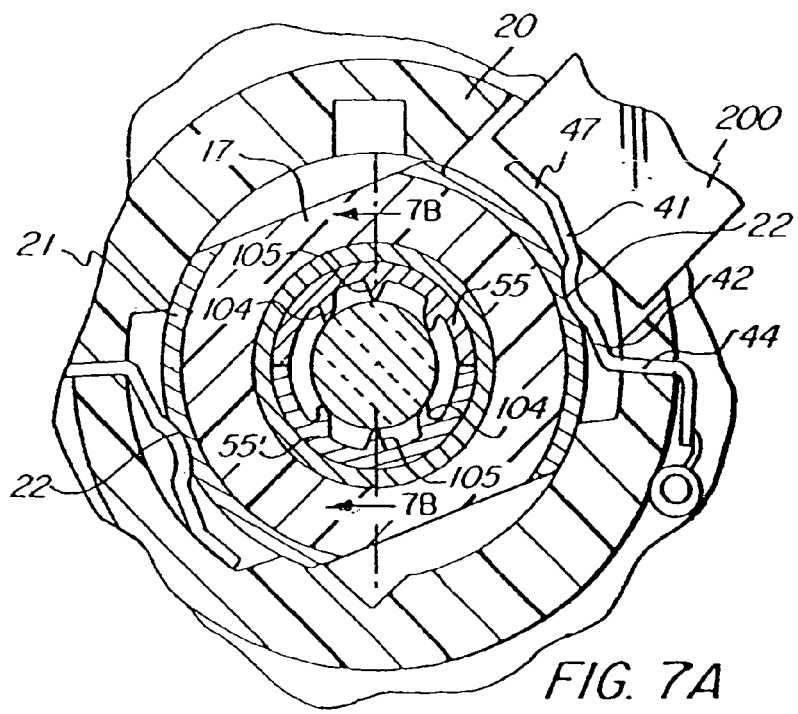
FIG. 7A is a sectional view of an interconnected plug and socket, showing an optical fiber within an optical fiber retainer in the plug, and showing supporting and positioning retainer rails and forward directed teeth.
Figure 7B:
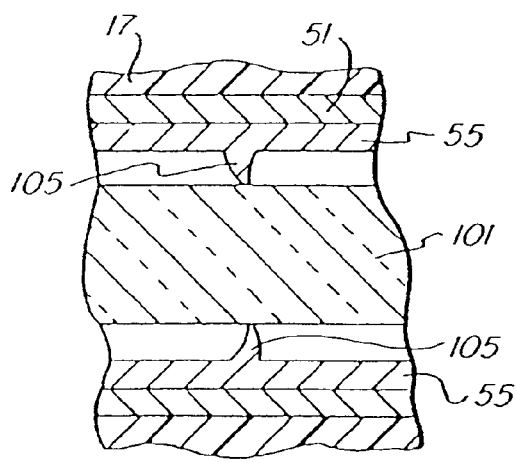
FIG. 7B is a sectional view taken along line 7B-7B in FIG. 7A.
Figure 8:
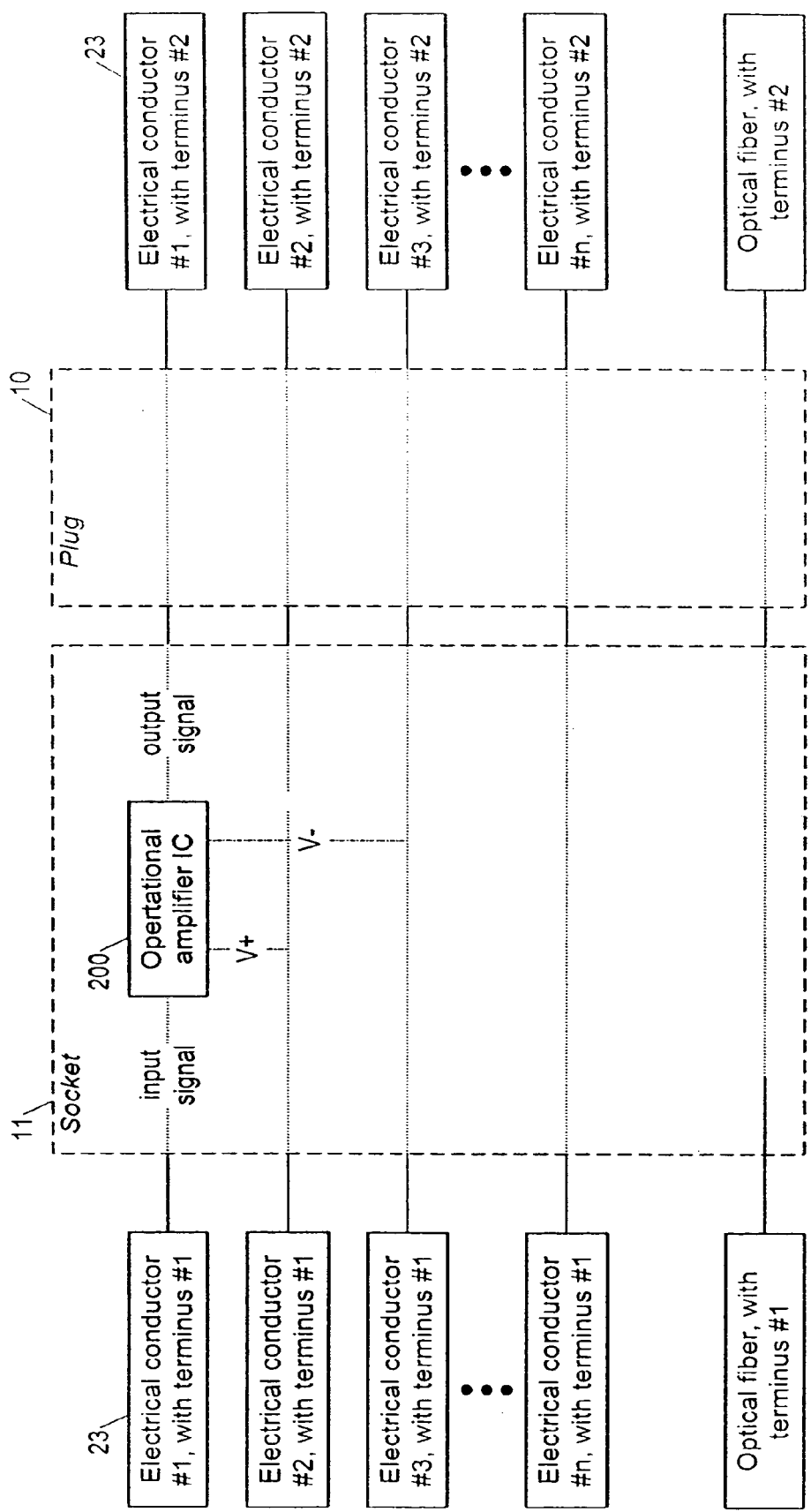
FIG. 8 is a block diagram of the connector shown in FIG. 1, showing the integrated circuit physically connected to and in series with an electrical connector having ends being connected by the connector.

Referring now to the drawings, and more particularly to FIGS. 1 to 4, 7A and 7B, and also FIG. 8, a connector demonstrating an especially advantageous embodiment of the invention is shown, including a plug 10 and a socket 11, with the socket 11 including an operational amplifier type of integrated circuit (IC) 200 in an opening 201 of the casing of the socket 11, through which the IC makes electrical contact with at least some of the conductors 23 having ends being joined by the connector, as shown in FIG. 6. The invention is to be understood to also encompass embedding an IC in the plug member of a connector having a plug member and a socket member, and also, in case of a splice connector (i.e. a permanent-type connection), having an IC integral with the splice connector. Thus, as mentioned, the connector shown in FIG. 1 is merely illustrative of the invention, although it is a preferred embodiment. The invention provides for use of any IC or solid state circuitry embedded in the body of any connector of any design or configuration.

The IC 200 is thus embedded in the connector 100 in that it is physically and electrically attached to the connector. Preferably, the IC 200 is actually buried in material of the socket 11, which is preferably a composite (insulator) material so as to be isolated from whatever environment the connector is used. Alternatively, the embedded IC 200 is disposed far enough into the casing or housing of the socket 11 so that a lid can close over it, covering the opening 201, and so making it easy to replace the IC in case it fails.

Plug 10 is formed of an insulating material such as thermoplastic or thermosetting resin and includes a longitudinally extending tubular shank 13 having a tapered frusto-conical leading end 14 and provided at its trailing end with an enlarged head 16, which defines a finger manipulating piece. Shank 13 is of substantially circular transverse cross-section and is provided with diametrically opposite longitudinally extending flat surfaces 17 extending from the tip 14 thereof to a point short of the head 16, flats 17 being closer to the axis of the shank 13 than the remaining arcuate (as in the arc of a bow) peripheral surface thereof.

Located on one of the arcuate surfaces of shank 13 adjacent tip end 14 are a pair of longitudinally spaced upright projections 18 having substantially parallel side walls, the forward projection being immediately posterior to the leading end 14 of the shank 13 and the rear projection being just forward of plug head 16. On the opposite arcuate surface of the shank 13 there may be located longitudinally spaced prismatic projections 19 which are diametrically opposite to the respective projections 18.

A set of longitudinally spaced and longitudinally aligned arcuate metal contact elements 20 are embedded in shank 13 along one of the arcuate peripheral surfaces thereof. The contact elements 20 extend circumferentially for less than 180° and their outer surface is coplanar with the arcuate peripheral surface of the shank 13 and their edges coplanar with flats 17. Another set of longitudinally spaced, longitudinally aligned arcuate contact elements 21 are provided, laterally aligned with the first set, the outer surfaces of elements 21 being coplanar with the arcuate surface of shank 13, the end edges of corresponding pairs of contact elements 20 and 21 being laterally spaced from each other. Formed in the outer surface of each of the contact elements 20 21 intermediate the ends thereof is an arcuate recess 22.

Connected to each of contact elements 20 and 21 is an insulator covered conductor 23, the end of which is soldered to a corresponding contact element, the conductors 23 being disposed along the inner peripheral base of shank 13 and extending longitudinally through the trailing end thereof.

Housed in and coaxial with shank 13 is a tubular strength member 50, preferably made of metal but also advantageously made from a hard plastic, which projects through the leading end of the shank 13, the insulated conductor 23 being sandwiched between the confronting faces of shank 13 and the tubular strength member 50. The leading end or section 51 of the tubular strength member 50 serves as a plug optical coupling member collar as described below and is delineated from the remainder of the tubular strength member 50 by inwardly and outwardly directed peripheral flanges respectively, flange 53 registering with a mating peripheral groove formed in the inner face of shank 13 to lock the strength member 50 against longitudinal movement.

The leading section 51 (FIG. 2) of the plug 10 defines the collar or sleeve of a plug optical coupling member 55 of an optical connector also including a mating socket optical coupling member 65 as described below, the plug optical coupling member 55 including an optical fiber retainer 56 with a leading end 56a. Retainer rails 104 (see especially FIGS. 7A and 7B), extend inward from the optical fiber retainer 56 and also extend longitudinally along the length of the retainer 56. An optical fiber 101 is located within and is coaxial with the optical fiber retainer 56, and terminates at the leading end 56a of the optical fiber retainer 56. Optical fiber 101 is supported in tube 50 by the optical fiber retainer 56 and the retainer rails 104, and also by teeth 105 (see especially FIGS. 7A and 7B) projecting inward and forward (in the direction of the leading end 56a). The teeth 105 prevent the optical fiber from backing into the plug 10, away from the leading end 56a.

The retainer rails 104 are made thin enough that they will give under pressure, as shown in FIG. 7B. The rails are preferably made of a soft metal (softer than the surface of the optical fiber) such as beryllium copper, so as to resiliently deform under pressure. The retainer rails 104 provide a radial centering force at four different but symmetrical places. The centering force tends to keep the optical fiber 101 centered in the optical fiber retainer 56. The optical fiber 101 is inserted into the plug 10 so that it slides along the retainer rails 104 until it protrudes slightly from the terminus of the plug 10, i.e. past the leading end 56a of the optical fiber retainer 56. The protruding optical fiber face is then ground flat and coplanar with the face of the optical fiber retainer leading end 56a and the leading end of the tubular strength member 50. The retainer rails 104 are also advantageously made of a plastic. The plastic is preferably one having a low coefficient of dynamic friction, allowing the optical fiber to be inserted into the plug 10 and pushed along the deformed rails until it reaches out past the leading end 56a of the optical fiber retainer 56. Alternatively, a plastic can be used in combination with a lubricant to allow inserting the optical fiber into the plug 10.

The socket 11 (see especially FIG. 3 and FIG. 4) includes a longitudinally extending inner shell 32 with interior surface defining a longitudinally extending cavity, the shell 32 preferably formed of an insulating plastic material in any well known manner and having at its trailing end an enlarged head 33 of hexagonal cross-section. A pair of oppositely disposed longitudinally extending grooves 34 and 36 respectively are formed in the inner face of the shell 32 and extend from the open trailing end thereof to a point short of the leading end. Groove 34 is of channel-shaped transverse cross-section corresponding in shape to the plug protuberance 18, and the groove 36 is of triangular transverse cross-section corresponding in shape to the plug protuberance 19, to permit sliding engagement between the corresponding grooves and plug protuberances and permitting sliding engagement between the plug and socket only at a predetermined orientation or polarization when the protuberances 18 and 19 register with the grooves 34 and 36. The relative sliding of the plug 10 and socket 11 is a non-shorting sliding in that the contacts of the plug do not touch the contacts of the socket during the sliding. (Of course instead of the plug member having protuberances and the socket member corresponding grooves, the protuberances and grooves can be on the other member of the connector, with the grooves in the plug disposed between the sets of contact elements 20 21.)

The grooves 34 and 36 (at their leading end) terminate in and communicate with circumferentially extending channel-shaped grooves as 37 (FIG. 1) extending approximately 90° clockwise as viewed forwardly from end 33. Also formed in the inner face of the shell 32 in the neighborhood of the head portion 33 (FIG. 4) are a pair of oppositely disposed channel-shaped circumferential grooves 38 extending clockwise from each of the longitudinal grooves 34 and 36 for approximately 90°. The longitudinal spacing between grooves 37 and 38 is equal to the longitudinal spacing between the plug protuberances 18 and 19. Thus, plug 10 may be inserted into socket 11 upon proper polarization, and following the full insertion of the plug within the socket, the plug may be rotated clockwise 90°, as viewed from the open end of the socket, the protuberances 18 and 19 engaging and locking in grooves 37 and 38.

Formed in the inner face of the inner shell 32 are two diametrically opposed longitudinal sets of circumferentially extending channel-shaped recesses 40 disposed between grooves 34 and 36. The center spacing between successive recesses 40 is substantially the same as the spacing between successive plug contact elements 20 or 21, and the recesses 40 of the opposite sets are laterally aligned. Disposed in each of recesses 40 is a contact element 41 formed of a resilient strip of metal. Each contact element 41 includes a curved section 42 having its convex portion directed inwardly towards the axis of shell 32 and provided with a centrally facing protuberance 43 adapted to engage recess 22 formed in the corresponding plug contact element 20 or 21. Radially projecting arm 44 extends from one end of the contact element curved portion 42 through the wall of inner shell 32 and terminates in a circumferentially extending contact (lug) 46 substantially superimposed upon the outer wall of inner shell 32. The free end of contact element curved portion 42 is oppositely bent, as at 47, and bears against the base of the corresponding recess 40. The crown of the contact element convex portion 42, as well as the protuberance 43, project inwardly of the inner cylindrical wall of the shell 32 when in normal unstressed condition. The contact elements 20 21 41 may be formed of any suitable conducting material such as brass or the like and are preferably electroplated in accordance with conventional practice with palladium or other suitable metal to provide greater corrosion-and abrasion-resistance and a better electrical contact surface.

The contacts 20 21 of the plug do not touch the contacts 41 of the socket during the sliding of the plug into the socket. Thus, as mentioned, the relative sliding of the plug 10 and socket 11 is a non-shorting sliding.

An intermediate cylindrical shell 49 (FIG. 3) is formed of an insulating material such as a plastic material, and may be integrally formed with the inner shell 32 or firmly adhered thereto. Contacts 46 of the contact elements 41 are embedded in the intermediate shell 49 and are connected to insulator covered conductors 75, which are also embedded in the intermediate shell 49 and extend longitudinally in the wall of the shell through the leading end thereof. It should be noted that the insulation covering 75 as well as that covering conductors 23 associated with the connector plug may be color-coded in the well-known manner. A tubular metal shell 51a (FIG. 4) tightly engages the intermediate shell 49, the leading edge thereof being inwardly inclined to engage the corresponding beveled surface of said intermediate shell, as in FIG. 3.

Embedded in the base or leading end of the shell 32 is the mate of the plug-carried optical coupling member 55 and includes a collar member 66, preferably made from metal for strength and resiliency. Located rearwardly of the base end of the collar 66 and formed integrally therewith are inwardly and outwardly directed peripheral flanges 67 and 68 respectively; flange 68 registering with a corresponding groove formed in shell 32. In addition, inwardly directed flange 67 has a further, thinner inwardly directed flange 310. Further inward flange 310 prevents inserting optical fiber 101 too far into socket 11 in the direction of the socket head 33 (FIG. 1).

Like the plug optical coupling member 55, the socket optical coupling member 65 also includes rails 104 and teeth 105 (see FIGS. 7A and 7B) projecting inward from an optical fiber retainer 56. In the case of the socket 11, the teeth 105 are directed toward the flanges 67 and 310 and so resist the optical fiber 101 from backing out of the socket once the optical fiber is inserted into the socket up to the innermost flange 310.

In coupling the plug and socket, plug 10 is aligned with and oriented relative to socket 11 so that the protuberances 18 and 19 engage the longitudinal grooves 34 and 36 respectively. As plug 10 is slid into socket 11, the flats 17 thereof confront the socket contact elements 41, whereas the plug contact elements 20 and 21 do not engage the contact elements 41 but merely slide along the inner surface of the insulating shell 32. When plug 10 is fully inserted in socket 11, the optical coupling member 55 is in engagement with the optical coupling member 65 and rotatable relative thereto. The optical fiber plug terminus 101a (see FIG. 2) is in near contacting registry with the optical fiber socket terminus 101b and collar 51 is in nesting contact with collar 66.

In order to effect engagement between the contact plug elements 20 and 21 and the socket contact elements 41, the plug is rotated clockwise, as seen in FIG. 7A. In this latter position, the plug and socket are in coupled contact closed position. As plug 10 is rotated relative to socket 11, the plug contact elements are conveyed along the socket contact elements 41 resiliently urging the latter forwardly until the contact recesses 22 are in registry with the contact protuberances 43, in which position the plug and socket are in contact closed position.

The reverse procedure is followed in effecting a contact open position and subsequently uncoupling the plug from the socket.

Instead of including in the connector 100 an optical coupling member 55 65 for coupling optical fibers, a coaxial connector can be included for coupling coaxial cables bearing radiofrequency (RF) signals, as shown and described in U.S. Pat. No. 3,154,360, entitled MULTI-CONDUCTOR COAXIAL ELECTRICAL CONNECTOR, issued Oct. 27, 1964, hereby incorporated by reference in its entirety. In such an embodiment, the connector 100 includes separable engagable conductor collar members and conductor pin elements coaxial with and mounted at the leading end of the plug 10 and at the base of the cavity and defining a coaxial connector, which is then in a coupled condition when the plug 10 is in its cavity advanced position within the socket 11. It is of course also possible to include within the connector 100 a plurality of RF or optical couplers for connecting a plurality of respective ends of pairs of RF and optical conductors as well as impedance-matching ICs.

In FIGS. 5 and 6 of the drawing, there is illustrated another embodiment of the present invention differing from that above described primarily in that a contact post 86 is provided on a plug 80 for facilitating connections thereto, it being understood that such expedient may be employed with the socket 11 shown in FIG. 1. In the embodiment shown in FIGS. 5 and 6, plug 80 includes the IC 200 in an opening 201 of a housing 89 for the contact post 86 (an IC that may be instead of or in addition to an IC embedded in the mating socket), and comprises a leading coupling section 81 similar in construction to plug 10 as above described, including a shank 82 carrying the contact elements 83 and an optical coupling member 84 in the manner earlier described. Coaxial with and projecting rearwardly from the trailing head end of the shank 82 is a tubular contact post 86, along the length of which is mounted a plurality of longitudinally and circumferentially spaced metal connector ears or contacts 87 provided with arms projecting through the wall of the contact post 86 into the interior thereof. Each of the contact elements 83 is electrically connected to a respective contact 87 by a corresponding conductor extending along the interior of shank 82 and contact post 86. An optical fiber 88 extends through contact post 86 and out its trailing end, and is connected to the optical coupling member 84 in the manner earlier described.

As shown in FIG. 5 and described above, it is here reemphasized that the embodiment of a plug member as shown in FIGS. 5 and 6 is one in which providing one or more ICs in the plug member instead of or in addition to providing ICs in the socket member is especially attractive; as shown in FIG. 5, an IC 200 is preferably embedded in the plug member 80 over the contact post 86 in the tubular housing 89.

The housing 89 for the contact post 86 is open-ended and tubular and has at least its inner face formed of an insulating material; it is slidable over contact post 86 with its peripheral wall radially spaced therefrom the leading inner border of the housing 89 separably snugly engaging an annular shoulder 90 formed on the trailing face of the plug head 91. Insulation covered conductors 92 have their ends soldered or otherwise connected to corresponding contacts 87 and together with the coaxial cable 88 extend through the trailing opening of the housing 89 and are connected as desired. Plug 80 may be employed with socket 11 as earlier described or with a socket modified in the manner of plug 80.

It is sometimes advantageous to plate the plug optical fiber face 101a and socket optical fiber face 101b using a thin layer of chromium, preferably 0.00025 inch. In such an embodiment, the closest approach of the two faces 101a and 101b of optical fiber is 0.0005 inch. In the preferred embodiment, however, the optical fiber faces 101a and 101b are not plated, because they do not actually abut since they are kept slightly separated by the thin inner flange 310 in the plug 11. In other embodiments where the optical fiber faces 101a and 101b would otherwise actually abut, using a thin plating of chromium (approximately 0.00025 inch on each face) will prevent cracking and spalling of the optical fibers being joined.

It is clear from the drawings and corresponding description that the present invention also comprehends a connector for simultaneously connecting a multi-conductor and not just a single optical fiber, but also several optical fibers. In such an embodiment, one optical fiber connection (i.e. both the plug and socket components for connecting two lengths of optical fiber) would act as a key for aligning the other optical fiber connections. In some applications, such a key optical fiber connection could be coaxial with the overall plug and socket. In other applications of the multi-conductor and multi-optical connector embodiment, the key optical fiber connection could be offset from the center of the plug. For example, in case of a connector for connecting two pairs of optical fiber lengths (to form two optical fibers), both optical fiber connections are advantageously offset from the center of the connector, with one of the optical fiber connections serving as a key. As in the preferred embodiment (FIGS. 2, 3, 4, 7A and 7B), each optical fiber connection would include (in both the plug and socket) an optical fiber retainer 56, rails 104, and teeth 105.

Referring now to FIGS. 9A-9C, the invention is shown as a connector 100a, for connecting ends of at least one conductor 23a suitable for conveying an electrical or an optical signal, the connector 100a having a plug end 10a and a socket end 11a to which respective ends of the conductor 23a are attached, and including one or another type of IC 200a-c disposed so as to be integral with the socket end 11a (although it is also possible for an IC to be embedded either instead or also in the plug end 10a, as illustrated in FIG. 5).

Referring now in particular to the embodiment shown in FIG. 9A, an impedance matching IC 200a is embedded in the socket 11a and obtains its supply voltage from a battery 210. The impedance matching IC 200a senses the input impedance of the plug end 10a and the (input) impedance of the socket end 11a (by techniques known in the art) and adjusts its own impedance so that the combined impedance of the plug end and the impedance matching IC 200a is substantially equal to the (input) impedance of the socket end 11a (not including the impedance matching IC 200*a*). In some embodiments there may be included in the socket end 11*a* separate resistive, capacitive and inductive elements, (separate from the impedance matching IC 200*a*) that the impedance matching IC 200*a* connects into the transmission path to match the impedance of the plug end 10*a* to that of the socket end 11*a*.

Referring now in particular to the embodiment shown in FIG. 9B, a controller IC 200*b*, i.e. an IC that performs the function of a controller in one or another application, is embedded in the socket 11*a* and also obtains its supply voltage from a battery 210. The controller IC 200*b* taps the signal on the conductor 23*a* to obtain an input signal, on the basis of which it provides an output signal that is shown being applied to an indicator 220 so as to convey information about the signal on the conductor 23*a*. The indicator could be, e.g., an LED. Alternatively, the output signal could be provided to a device that performs a function upon receiving a predetermined signal. For example, the output signal could be provided to a thermostat control device that adjusts a thermostat based on the voltage of the output signal.

Referring now in particular to the embodiment shown in FIG. 9C, a general purpose microprocessor IC 200*c* is embedded in the socket 11*a*, and instead of obtaining its supply voltage from a battery 210, it does so via special supply voltage lines 230. Like the controller IC 200*b*, the microprocessor IC 200*c* taps the signal on the conductor 23*a* to obtain an input signal, on the basis of which it provides an output signal that is shown being applied to an indicator 220 so as to convey information about the signal on the conductor 23*a*. A typical microprocessor would ordinarily have several inputs, one from each of several different conductors being connected by the connector, such as the conductor 23*a*, not simply one input as shown in FIG. 9C; only a single input is shown there purely for ease of illustration. The microprocessor IC 200*c* differs from the controller IC 200*b* both in the number of inputs and in the complexity of the processing it performs. The output of the microprocessor IC 200*c* is shown again being provided to an indicator 220, as in the embodiment shown in FIG. 9B, but ordinarily the indicator being provided with an input by the microprocessor IC 200*c* would be capable of providing substantially more information than the indicator being provided with an input by the controller IC 200*b*.

As mentioned above, the invention also comprehends having an IC embedded in a splice, i.e. a connector not having a plug and a socket, but which connects two ends of a conductor by itself providing a conducting medium and by holding the two ends of the conductor in a way that makes electrical or optical contact. In such an embodiment, the IC is embedded in the splice so that when one or another of the ends of the conductor being joined are inserted into the splice, whatever contact is required between the IC and the conductor results unavoidably. For example, if the IC is inline, then by inserting into the splice the two ends of the conductor being joined by the splice, the two ends make (electrical or optical) contact with the input and output terminals of the IC. (An inline IC must of course be embedded in the splice, including being physically and electrically attached to the splice, so that the conductor being spliced includes the inline IC as the only path through which the signal being conducted can follow from one end of the spliced conductor to the other.) In splice embodiments, the power for the IC is preferably (and most simply) provided by a battery also embedded in the splice, although the power can also be provided by an external source, such as a battery not embedded in the splice or by an external power supply, or even by taps from other conductors also inserted into the splice.

As also mentioned above, the embedded IC can be for use as part of an optical circuit. For example, it can be a repeater/amplifier. Such an IC can be powered using power conveyed via an optical conductor, as indicated in FIG. 10, or power conveyed via electrical conductors, as in FIG. 11. (In FIG. 10, the IC 200 is shown powered by tapping a single optical conductor, an arrangement that would be possible for example for an IC including a photovoltaic cell, not shown, and so providing the customary V+ and V− inputs typically required by an IC.) In case of more than one optical conductor feeding to a member (either the plug or socket) of the connector, the connector illustrated in FIG. 1 can be adapted so as to connect a plurality of optical conductors, or so as to provide power in the form of light via an optical conductor terminating in one or another member of the connector, analogously to how the electrical connectors 230 of FIG. 9*c* provide power in the form of an electrical current. In addition, what is not shown but also contemplated is having an embedded IC used in connection with an electrical circuit being powered by power conveyed by optical conductors.

A connector according to the invention has been described above as including an IC embedded in the connector—i.e. buried in the material of the housing or casing of the connector—so as to be a part of, or integral with, the connector. Also in the embodiments so far described, an embedded IC associated with a pair of conductors being connected by a connector according to the invention has been shown as physically attached in line with at least one of the conductors being connected which, when connected, are themselves physically attached, so that the IC ends up physically attached in line with the two conductors when the plug and socket are mated. In addition to what is described above, though, the invention also encompasses a connector including an IC embedded in the connector, as above, and electromagnetically (including optically) coupled to a conductor being connected by the connector to another conductor as above, but not physically attached to the conductor or to the other conductor. In such other embodiments of the invention, the IC is, according to the invention, indirectly coupled—via an electromagnetic field—to a connector in either one or the other of the two housings of the connector. Further, the inventions is not limited to such indirectly coupled ICs only when embedded in a connector, but instead encompasses such indirectly coupled ICs generally.

For example in respect to the indirect coupling, an IC in a connector according to the invention can be capacitively or inductively coupled to a conductor of the connector in case of a conductor providing a path for an electrical signal (including RF), or it can be optically coupled to a conductor of the connector in case of a conductor providing a path for an optical signal. Such indirect coupling is advantageous for different reasons in different applications: an advantage in some applications is that a connector with such a coupling to an IC can be more easily repaired in the field in case of damage to the conductor indirectly coupled to the IC (because the conductor can be replaced or repaired without having to physically reconnect it to the IC).

An embedded, indirectly coupled IC can be used for many different applications, and in particular is of use as a test circuit. For example, an indirectly coupled IC can sense a signal in a conductor within a first housing of a connector and being joined to another conductor in a second housing, and can respond by producing a signal that provides diagnostic information. The signal bearing the diagnostic information can be coupled back to the conductor in the first housing, or can be provided on another line entirely. Also, since the indirectly coupled IC is in fact (electromagnetically even though not mechanically) coupled to the conductor, it affects the input impedance of the conductor, and so can be used for impedance matching. Other applications, such as mentioned above, are also possible.

It should be understood that the invention also encompasses embodiments in which—in connecting two conductors, one terminated in one housing of a connector according to the invention and the other in the other housing—the connector does not physically necessarily mate the two ends of the conductor, and instead, the ends of the conductors terminate in an insulator medium (including e.g. air). Such insulator-terminated conductors (as opposed to conductors that are physically connected when the plug and socket are joined) are still able to bear a signal; for example, a simple antenna could be said to be such an insulator-terminated conductor. In embodiments in which the conductors being "connected" are insulator-terminated, the signals on the two conductors can be different, and so ICs that perform operations on a signal over a period of time and then produce a new, processed signal, are also possible.

In making a connector according to an embodiment in which the conductors are insulator-terminated, the IC is typically coupled to both connectors, to one for input, and to the other for output. Both couplings should of course be made as efficient as possible, but it is of course more important to optimize the coupling to the conductor conveying the output. Therefore, the IC is advantageously located in the housing in which the conductor conveying the output is terminated. Further, depending on the kind of signal being conveyed—i.e. the frequency of the signal, and so whether it is optical, microwave, RF, or lower frequency electromagnetic signal—the coupling is different in kind. For example, for relatively low frequency signals compared to optical signals—i.e. including RF but also including lower frequency electromagnetic signals, usually called simply AC signals—the coupling can be capacitive or inductive. For RF and microwave, the coupling can instead be accomplished using an antenna, and preferably a highly directional antenna. For optical, the coupling can be similar to what would be used in case of physically attached conductor ends, but since the coupling in insulator-terminated conductors is indirect, the coupling is inevitably less efficient, and yet it is still useful to have insulator-terminated optical conductors (which are isolated, one from the other, since they are not physically attached) for the same reason as in case of non-optical signals: ease of repair in the field.

Referring now to FIGS. 12A-12B, the invention is shown in case of an indirectly coupled IC as a connector 300, for connecting ends 301a 301b of two conductors 323a 323b, which, when connected, are suitable for conveying an electrical or an optical signal, the connector 300 having a plug end 10a and a socket end 11a to which respective ends of the conductor 23a are attached as described above, and including one or another type of IC 200 disposed so as to be embedded in, and so integral with, the socket end 11a, but here not mechanically attached to either of the conductors 301a 301b, and instead including at least a local coupler 302a for coupling to the conductor 323a in the housing 11a in which the IC 200 is embedded (the socket housing in this case). In FIG. 12A, the respective ends 301a 301b of the two conductors 323a 323b are, as above, indicated by connection 320 as being placed in mechanical contact by the connector 300. In FIG. 12B on the other hand, even when in the "connected" state shown in FIG. 12B, the two conductors 323a 323b do not touch, and the connection is provided via the IC 200 and two couplers 302a 302b, a local coupler 302a for coupling to the conductor 323a in the same housing as the IC 200, i.e. the socket, and a far coupler 302b for coupling to the conductor 323b in the other housing 10a, i.e. the plug.

The conductors in FIG. 12B are therefore, in the terminology introduced above, insulator-terminated, and the far coupler senses the signal in the conductor 323a in the plug 10a, provides it as an input to the IC 200, which provides a corresponding output to the local coupler 302a in the plug 11a with the IC 200, and the local coupler 302a then feeds the signal to the conductor 323b in the plug 11a. With the arrangement of FIG. 12B, the two conductors 323a 323b can carry different signals, whereas in FIG. 12A, since the two conductors 323a 323b mechanically touch, they are not isolated, and both carry the same signal.

As mentioned above, the couplers 302a 302b can be of various types, but all rely on one or another type of field/indirect coupling to the conductors 323a 323b, and neither makes mechanical contact with either of the conductors 323a 323b.

As in the above-described embodiments (e.g. in FIGS. 8, 9A-C, and 10-11) in which the IC is mechanically connected to one or more of the two conductors in the pair of conductors 23a in respective housings of the connector 100a, a connector according to the embodiments illustrated generally in FIGS. 12A and 12B can also connect a plurality of conductors, and further, the IC 200 can tap one or more of the conductors for power, rather than relying on a battery as in FIGS. 12A and 12B.

It should be appreciated that the invention encompasses not only connectors of ordinary scale, but also nanotechnology-scale connectors, i.e. microscopic connectors made out of individual molecules or small numbers of molecules (and also hybrid connectors—i.e. part ordinary scale and part nanoscale, having housings and perhaps some conductors of ordinary scale, but including at least some nanotechnology-scale components). In such embodiments, the IC 200 and the (near and far) couplers 302a 302b can be nanotechnology devices. In such embodiments, therefore, the difficulties present in achieving effective near and far coupling are significantly less than in a connector according to the ordinary scale of connectors. Further, in such embodiments, the power transfer by the couplers can be quite small, and yet still be highly useful.

More specifically, in nano-connectors according to the invention, the (near and far couplers) 302a 302b can be based on e.g. so-called carbon nanotubes, which can serve as antennae attuned to specific frequencies. Carbon nanotubes are long, thin cylinders of carbon, which are actually large macromolecules. They can be considered to be a sheet of graphite—that is actually a hexagonal lattice of carbon—rolled into a cylinder. Besides having a single cylindrical wall, nanotubes can have multiple walls—cylinders inside the other cylinders.

More generally, an IC 200 according to the invention (and so indirectly coupled to a conductor) comprises transistors made out of what are sometimes called electromagnetic materials (materials that advantageously interact with electromagnetic fields) including so-called nanofibers (some of which are sometimes also called "Bucky Fibers", referring to the nanofibers derived from the 60-carbon Fulerene molecule), and also comprising magnetically bonded materials.

The state of the art of nanotechnology has developed significantly in the years since Richard P. Feynman introduced the idea of nanotechnology in 1959. For example, AMBIT Corporation (of Ashland, Mass.) has now developed nanotube technology for precisely placing, growing, and tuning application-specific nanowires directly into junctions and other substrates, making it possible for designers to fabricate lightwave-scaled band gap and antenna structures, circuits and electro-optical devices conveniently and quickly using techniques that are largely compatible with standard semiconductor processing techniques. Devices that are enabled by current carbon nanotube technology include: detectors in which nanowires are grown directly on top of semiconducting surfaces and junctions, with the orientation and position of the nanostructures chosen so as to provide the sensitivity and selectivity needed for an application (and in which each nanowire, or group of nanowires can be tuned, so that frequency selectivity can be tailored for each application); optical harmonic emitters, for collecting and emitting electromagnetic energy, including lightwave energy, at harmonic multiples (with applications including efficient solid state broad band lighting, UV (ultraviolet) generation, RFID (radio frequency identification) and optical identification and tracking systems); frequency conversion devices, i.e. mixers (optical and electronic); switching and beam steering devices in which, when nanoscale elements are positioned in the right way, the antenna-like operation of the nanoscale elements and the ability to switch and/or bias them, allows rapid redirection and reinforcement of single and multiple optical wavefronts (useful e.g. in high-speed routing of optical signals without mirrors or other electromechanical devices).

Besides the use of nanoscale components in the connectors of FIGS. 12A and 12B, the invention also encompasses nanoscale components in which the embedded IC is physically connected to the connector whose two parts are connected by the connector, as shown most clearly in FIGS. 8, 9A-C, 10 and 11. Nanoscale connectors (or connector components) are in general advantageous whenever trying to provide a connection for low (and very low) current levels.

In nanoscale embodiments, the embedded IC itself can be nanoscale, as opposed to embodiments in which only the couplers are nanoscale. In such embodiments, the IC can be e.g. an integration of diodes, transistors, and simple logic gates based on self-assembly using DNA (deoxyribonucleic acid). DNA has recently been shown to have all the components needed to build an electronic device as well as the self-assembly characteristics needed to form complex electronic circuits (and then even to perform self-replication).

The embedded ICs of the connector embodiments of FIGS. 8, 9A-C, 10 and 11, as well as the electromagnetic coupling and embedded IC on which the invention is based in the embodiments illustrated in FIGS. 12A and 12B all advantageously use superconducting components, even in case of nanoscale embodiments. For example, researchers in Hong Kong have recently created one-dimensional, single-walled carbon nanotubes having some superconducting traits (when isolated and highly aligned, with a transition to superconducting behavior at around a relatively high 15 degrees Kelvin, a much higher temperature than for superconductivity observed in nanotube bundles). In general, superconducting components are more advantageous for higher current levels through the connector, but are also useful even in case of nanoscale embodiments not because any significant amount of energy is saved—as indeed it is not in such embodiments—but instead because of the improvement in performance that results generally.

Nothing that has been said limits the invention to the use of ICs having couplers that couple to conductors indirectly only in connectors, and as mentioned, the invention encompasses the use generally of such ICs having couplers for indirect coupling, in any electrical or optical circuit. The invention even encompasses the use of ICs with couplers for indirect coupling in applications within a human or non-human animal. For example, the invention, with the ICs and couplers in nanoscale, is of use in a synapse for providing connectivity between neurons terminating in the synapse, when the neurotransmitters normally released into the synapse by one of the neurons terminating there and which normally provide the connectivity, are not released. In such an application, the neurons are the conductors to which the couplers (a local and far coupler) electromagnetically couple.

In another application, an IC and a coupler are of use in a circuit for providing control of heart fibrillation, i.e. as components of e.g. an automatic implantable defibrillator/cardioverter, commonly referred to as an AICD, which is a device that continuously monitors the heart rhythm. If an AICD detects an abnormally fast heart rhythm, it either electrically paces the heart very fast or delivers a small electrical shock to the heart to convert the heart rhythm back to normal. In such an application, in some embodiments, the invention provides an IC and a sensing coupler, and both the IC and the sensing coupler can be nanoscale, with the sensing coupler acting as an antenna and sensing heart activity by sensing electrical signals generated by the heart itself in the sinus node, which then propagate through the atria and then ultimately, at least in part, through the ventricles, via the so-called AV disc. In such an application, any parts of the atria, ventricles, or AV disc can serve as the conductors to which an IC according to the invention is indirectly coupled via a coupler. Here, in embodiments in which both the IC and sensing coupler are nanoscale, the output of the IC can be provided to conventional equipment for actually pacing the heart or the IC can itself provide the pacing via a second, pacing coupler. It is likely that the small shock to the heart would be provided by a signal from the IC to equipment of more normal scale, though. Instead of both the IC and coupler being nanoscale, though, in some applications it may be advantageous for only the sensing coupler to be nanoscale, in which case both the pacing and shock can be provided by the IC, rather than have the IC signal other equipment for providing the shock stimulus.

Thus, and now referring to FIGS. 13A-B, the invention encompasses also an apparatus 130 including an IC 200, at least a local coupler 302A, and possibly also a far coupler 302B, with the couplers configured to electromagnetically couple to one or more conductors 323a 323b, but not necessarily including a housing or housings 10a 11a (the housings indicated as a plug and socket in FIGS. 12A and 12B). Moreover, the conductors 323a 323b can be man-made or naturally occurring in a human or non-human animal.

In the above description, the terminology "indirectly coupled" or "electromagnetically coupled" is used to indicate how an IC according to the invention is coupled to a conductor or, more accurately, to a signal being conveyed by a conductor. The terminology "indirectly coupled" or "electromagnetically coupled" should be understood here as meaning that the IC is separated from the conductor by a gap filed by air or some other insulator, and that under normal operating conditions, no charge carriers (including holes in semiconductors) pass across the gap from the conductor to the IC or vice versa. In case of capacitive coupling, there is a so-called displacement current that is said to flow across an insulator gap from one conductor of the capacitor to the other, but a displacement current is not a current in the ordinary sense (charge carriers do not in fact traverse the insulator gap), and coupling via a displacement current is encompassed by the invention.

Further, although the terminology "electromagnetically coupled" is often used in the above description, it should be understood that the coupling need not rely on sensing or communicating both the electric and magnetic component of an electromagnetic field; the coupling can rely on sensing only either one or the other (just as some antennas sense only the electric component, and some others only the magnetic component of an electromagnetic field).

Further still, the invention has been described above in terms of an IC indirectly coupled to a signal conveyed by a conductor, and it should be understood that the coupling can be to any kind of signal that provides an electric or magnetic field. Thus, the signal is not necessarily a signal based on the flow of electric charge, i.e. an electronic signal, but can also be what is today called a spintronic (spin-electronic) signal, also sometimes called a magnetoelectronic signal. Spintronics refers to the use of phenomena involving electron spin, and more generally nuclear spin, and possibly also the charge of the particle, at least in cases the particle has charge. (A neutral particle can have a spin that can be sensed (as a corresponding magnetic field/magnetic moment). For example, a neutron, which is electrically neutral, has a spin associated with a measured magnetic moment; the magnetic moment is thought to result from a current distribution within the neutron.) Thus, a signal can be conveyed via a spintronic current. For example, a conductor could provide a path for the flow of electrons in which signalling is provided not only by the (net) charge per unit time passing through a point of the conductor, but also based on the (net) spin passing through the point of the conductor. The purely spin component of the signal (i.e. the spin current) could be detected as a variation in the magnetic field associated with the ordinary current (i.e. the charge current). In principle, two different currents could be conveyed by the same conductor, one with spin up and one with spin down, thereby doubling the bandwidth of the conductor.

The invention also encompasses the use of components within the IC that rely on spintronic phenomena, i.e. components that specifically exploit spin properties instead of or in addition to charge. (Both ordinary scale technology and nanotechnology make use of spintronic phenomena.) For example, for its coupling to a conductor, the IC could rely on spin relaxation and spin transport. One specific spintronics application is in a read head and a memory-storage cell: a giant-magnetoresistive (GMR) sandwich structure having alternating ferromagnetic and nonmagnetic metal layers is used. Depending on the relative orientation of the magnetizations in the magnetic layers, the device resistance changes from small (when the magnetizations are aligned, i.e. parallel) to large (antiparallel magnetizations). Such a change in resistance can thus be used as a basis for sensing changes in magnetic fields, and so for sensing (ordinary or spintronic) current in a conductor. (GMR can also be used as the basis for providing a spin current valve, by changing the orientation of the magnetization of at least one of the magnetic layers, which would then act on the spin carriers permitting a spin carrier to pass through if the spin is aligned with that of the magnetic layer, but not if otherwise.)

It is to be understood that the above-described arrangements are only illustrative of the application of the principles of the present invention. Numerous other kinds of ICs are comprehended, and numerous modifications and alternative arrangements to those described above may be devised by those skilled in the art without departing from the scope of the present invention, and the appended claims are intended to cover such other kinds of ICs, modifications and arrangements, and in particular the use of nanotechnology in various and all respects.

What is claimed is:

1. A connector, comprising:
 a first housing for receiving an end portion of a first conductor;
 a second housing for receiving an end portion of a second conductor; and
 wherein the connector is configured to provide a connection between the first conductor and the second conductor for propagation of a signal from the first conductor to or from the second conductor;
 and further comprising at least one integrated circuit mechanically attached to or included in the first housing, and directly or indirectly connected to the first conductor so as to directly or indirectly couple to the signal;
 and further wherein the connector is configured to use as a supply voltage for the integrated circuit a voltage provided at least in part from the connection to the first conductor or from a connection to another conductor also having an end portion received by the first housing.

2. The connector of claim 1, wherein the connector is configured so that power for the integrated circuit is provided by a tapping of the first conductor.

3. The connector of claim 1, wherein the connector is configured so that power for the integrated circuit is provided by supply voltage lines terminated in the connector.

4. The connector of claim 1, wherein the connector is configured to provide a connection of the first conductor to the second conductor with the integrated circuit disposed in line in the connection so that all of the signal traverses the integrated circuit.

5. The connector of claim 4, wherein the connection comprises a direct connection of the first conductor to the integrated circuit and a direct connection of the integrated circuit to the second conductor.

6. The connector of claim 4, further comprising at least a first coupler connected to the integrated circuit, and wherein the connection of the first conductor to the second conductor includes a direct connection of the first conductor to the integrated circuit, and an indirect connection of the integrated circuit to the second conductor mediated by the coupler.

7. The connector of claim 6, wherein either the coupler provides capacitive coupling or the coupler provides inductive coupling.

8. The connector of claim 6, wherein the coupler includes an antenna for providing electromagnetic coupling.

9. The connector of claim 6, wherein the coupler includes a directional optical coupler.

10. The connector of claim 6, wherein at least either the integrated circuit or the coupler includes nanoscale elements.

11. The connector of claim 6, wherein the coupler includes a nanoscale antenna.

12. The connector of claim 11, wherein the nanoscale antenna includes a carbon nanotube.

13. The connector of claim 4, wherein the connector includes a second coupler connected to the integrated circuit, and further wherein the connection of the first conductor to the second conductor includes a first indirect connection of the first conductor to the integrated circuit via the first coupler, and a second indirect connection of the integrated circuit to the second conductor via the second coupler.

14. The connector of claim 1, wherein the connection comprises a direct connection of the first conductor to the second conductor and the integrated circuit is connected to the first conductor via an indirect connection mediated by a coupler connected to the integrated circuit, thereby providing a connection for a signal path from the first conductor to the second conductor not including the integrated circuit.

15. The connector of claim 1, wherein the signal is an electric signal.

16. The connector of claim 1, wherein the signal is an alternating current electric signal.

17. The connector of claim 1, wherein the signal is a radio frequency signal.

18. The connector of claim 1, wherein the signal is a microwave signal.

19. The connector of claim 1, wherein the signal is an optical signal.

20. The connector of claim 1, wherein the signal is a spintronic current.

21. The connector of claim 1, wherein the integrated circuit is an amplifier.

22. The connector of claim 1, wherein the integrated circuit is an impedance matching circuit.

23. The connector of claim 1, wherein the integrated circuit is a test and evaluation circuit for testing connectivity through the connector.

24. The connector of claim 1, wherein the integrated circuit provides a repeater function for a digital signal.

25. The connector of claim 1, wherein the connector includes an indicator for displaying a signal indicating an output of the integrated circuit.

26. A connector as in claim 1, wherein the integrated circuit includes nanoscale elements.

27. A connector as in claim 1, wherein the integrated circuit includes superconducting elements.

28. The connector of claim 1, wherein the integrated circuit is a circuit for suppressing crosstalk.

* * * * *